(12) United States Patent
Mulrooney

(10) Patent No.: US 12,582,821 B2
(45) Date of Patent: Mar. 24, 2026

(54) DEVICES, SYSTEMS, AND METHODS FOR TREATING DISEASE USING ELECTRICAL STIMULATION

(71) Applicant: Phagenesis Limited, Manchester (GB)

(72) Inventor: Conor Mulrooney, Manchester (GB)

(73) Assignee: Phagenesis Limited, Manchester (GB)

( * ) Notice: Subject to any disclaimer, the term of this patent is extended or adjusted under 35 U.S.C. 154(b) by 370 days.

(21) Appl. No.: 18/253,516

(22) PCT Filed: Nov. 19, 2021

(86) PCT No.: PCT/GB2021/053011
§ 371 (c)(1),
(2) Date: May 18, 2023

(87) PCT Pub. No.: WO2022/106844
PCT Pub. Date: May 27, 2022

(65) Prior Publication Data
US 2023/0405324 A1 Dec. 21, 2023

Related U.S. Application Data

(60) Provisional application No. 63/198,881, filed on Nov. 19, 2020.

(51) Int. Cl.
*A61N 1/36* (2006.01)
*A61N 1/05* (2006.01)

(52) U.S. Cl.
CPC ....... *A61N 1/36103* (2013.01); *A61N 1/0551* (2013.01)

(58) Field of Classification Search
None
See application file for complete search history.

(56) References Cited

U.S. PATENT DOCUMENTS

| | | | |
|---|---|---|---|
| 803,464 | A | 10/1905 | Beck |
| 1,032,436 | A | 7/1912 | Smith |

(Continued)

FOREIGN PATENT DOCUMENTS

| | | |
|---|---|---|
| CA | 2594296 A1 | 3/2006 |
| CN | 203389196 U | 1/2014 |

(Continued)

OTHER PUBLICATIONS

Wilmskoetter, Janina, et al., "Cortical and Subcortical Control of Swallowing—Can We Use Information From Lesion Locations to Improve Diagnosis and Treatment for Patients With Stroke?", American journal of speech-language pathology vol. 29,2S (2020): 1030-1043. (Year: 2020).

(Continued)

*Primary Examiner* — Michael W Kahelin
(74) *Attorney, Agent, or Firm* — Fortem IP LLP

(57) ABSTRACT

Electrical stimulation devices and associated systems and methods are disclosed herein. In some embodiments, the electrical stimulation device comprises an elongated member configured to be orally or nasally inserted into a patient's pharynx. The device may further include a conductive element carried by a distal portion of the elongated member and configured to deliver stimulation energy to nearby tissue. A stiffness of the elongated member may vary along its length to facilitate insertion of the elongated member through the nasopharyngeal junction and provide a restoring force necessary to hold the conductive element in apposition with tissue at the treatment site.

25 Claims, 6 Drawing Sheets

(56) References Cited

U.S. PATENT DOCUMENTS

| | | |
|---|---|---|
| 2,627,096 A | 2/1953 | Alessi |
| 2,779,985 A | 2/1957 | Turner et al. |
| 3,179,995 A | 4/1965 | Hawk |
| 3,630,195 A | 12/1971 | Santomieri |
| 3,839,841 A | 10/1974 | Amplatz |
| 3,894,706 A | 7/1975 | Mizusawa |
| 3,951,136 A | 4/1976 | Wall |
| 4,025,015 A | 5/1977 | Kolic |
| 4,295,618 A | 10/1981 | Morota et al. |
| 4,381,011 A | 4/1983 | Somers |
| 4,453,545 A | 6/1984 | Inoue |
| 4,531,937 A | 7/1985 | Yates |
| 4,691,883 A | 9/1987 | Kurihara |
| 4,707,906 A | 11/1987 | Posey |
| 4,776,349 A | 10/1988 | Nashef et al. |
| 4,840,337 A | 6/1989 | Zaugg |
| 4,960,412 A | 10/1990 | Fink |
| 5,109,870 A | 5/1992 | Silny et al. |
| 5,125,904 A | 6/1992 | Lee |
| 5,147,315 A | 9/1992 | Weber |
| 5,179,952 A | 1/1993 | Buinevicius et al. |
| 5,201,903 A | 4/1993 | Corbett et al. |
| 5,372,131 A | 12/1994 | Heinen |
| 5,382,239 A | 1/1995 | Orr et al. |
| 5,389,074 A | 2/1995 | Parker et al. |
| 5,457,852 A | 10/1995 | Liu |
| 5,546,938 A | 8/1996 | McKenzie |
| 5,551,953 A | 9/1996 | Lattin et al. |
| 5,588,424 A | 12/1996 | Insler et al. |
| 5,755,225 A | 5/1998 | Hutson |
| 5,759,490 A | 6/1998 | Malchesky |
| 5,762,638 A | 6/1998 | Shikani et al. |
| 5,800,402 A | 9/1998 | Bierman |
| 5,833,663 A | 11/1998 | Bierman et al. |
| 5,836,895 A | 11/1998 | Ramsey |
| 5,957,968 A | 9/1999 | Belden et al. |
| 6,006,138 A | 12/1999 | Don |
| 6,148,222 A | 11/2000 | Ramsey |
| 6,259,938 B1 | 7/2001 | Zarychta et al. |
| 6,266,548 B1 | 7/2001 | Lamade et al. |
| 6,366,813 B1 | 4/2002 | DiLorenzo |
| 6,464,697 B1 | 10/2002 | Edwards et al. |
| 6,484,053 B2 | 11/2002 | Leelamanit et al. |
| 6,532,388 B1 | 3/2003 | Rakow et al. |
| 6,611,699 B2 | 8/2003 | Krueger |
| 6,613,025 B1 | 9/2003 | Palasis |
| 6,658,294 B1 | 12/2003 | Zadeh et al. |
| 6,804,866 B2 | 10/2004 | Lemke et al. |
| 6,856,822 B2 | 2/2005 | Larsson |
| 7,191,017 B1 | 3/2007 | Koop et al. |
| 7,324,851 B1 | 1/2008 | DiLorenzo |
| 7,598,839 B1 | 10/2009 | Wedley |
| 7,871,430 B2 | 1/2011 | Pavcnik et al. |
| 7,918,828 B2 | 4/2011 | Lundgaard et al. |
| 8,048,062 B2 | 11/2011 | Adams et al. |
| 8,092,433 B2 | 1/2012 | Hamdy |
| 8,876,798 B2 | 11/2014 | Clark et al. |
| 8,968,331 B1 | 3/2015 | Sochor |
| 9,895,486 B1 | 2/2018 | Carey-Hench |
| 9,982,742 B2 | 5/2018 | Loewe et al. |
| 10,028,885 B2 | 7/2018 | Martin et al. |
| 10,285,341 B2 | 5/2019 | McCaslin et al. |
| 10,743,810 B2 | 8/2020 | Mulrooney |
| 10,888,690 B2 | 1/2021 | Mulrooney |
| 11,617,881 B2 | 4/2023 | Mulrooney et al. |
| 11,980,753 B2 | 5/2024 | Mulrooney et al. |
| 11,992,681 B2 | 5/2024 | Mulrooney |
| 12,419,568 B2 | 9/2025 | Mulrooney |
| 12,420,084 B2 | 9/2025 | Mulrooney et al. |
| 2001/0039413 A1 | 11/2001 | Bowe |
| 2001/0054425 A1 | 12/2001 | Bertram |
| 2002/0032468 A1 | 3/2002 | Hill et al. |
| 2002/0065544 A1* | 5/2002 | Smits ................... A61N 1/0563 |
| | | 607/122 |
| 2002/0157673 A1 | 10/2002 | Kessler et al. |
| 2002/0165537 A1 | 11/2002 | Kelley et al. |
| 2002/0177765 A1 | 11/2002 | Bowe et al. |
| 2003/0036794 A1 | 2/2003 | Ragheb et al. |
| 2004/0034396 A1 | 2/2004 | Asmar et al. |
| 2004/0073110 A1 | 4/2004 | Stewart et al. |
| 2004/0162584 A1 | 8/2004 | Hill et al. |
| 2004/0220645 A1 | 11/2004 | Kretschmer et al. |
| 2004/0230162 A1 | 11/2004 | Tan |
| 2005/0098688 A1 | 5/2005 | Miarka et al. |
| 2005/0137459 A1 | 6/2005 | Chin et al. |
| 2005/0146676 A1 | 7/2005 | Silvestro |
| 2005/0192559 A1 | 9/2005 | Michels et al. |
| 2005/0229933 A1 | 10/2005 | McGrail et al. |
| 2006/0085049 A1 | 4/2006 | Cory et al. |
| 2007/0074728 A1 | 4/2007 | Rea |
| 2007/0089898 A1 | 4/2007 | Potter |
| 2007/0156041 A1 | 7/2007 | Rea |
| 2008/0009810 A1 | 1/2008 | Hamdy |
| 2008/0147013 A1 | 6/2008 | Breton et al. |
| 2008/0249507 A1 | 10/2008 | Hadani |
| 2008/0255441 A1 | 10/2008 | Hadani |
| 2008/0300530 A1 | 12/2008 | Massengale |
| 2009/0062772 A1 | 3/2009 | Wakeford et al. |
| 2009/0223698 A1 | 9/2009 | Gilliland et al. |
| 2009/0275825 A1 | 11/2009 | Thomas |
| 2009/0276025 A1 | 11/2009 | Burnes et al. |
| 2010/0115739 A1 | 5/2010 | Mathur |
| 2010/0170066 A1 | 7/2010 | Honeycutt |
| 2010/0174170 A1 | 7/2010 | Razavi |
| 2010/0206453 A1 | 8/2010 | Leeflang et al. |
| 2010/0218975 A1 | 9/2010 | Mehan |
| 2010/0317956 A1 | 12/2010 | Kartush |
| 2011/0137374 A1 | 6/2011 | Kieval et al. |
| 2011/0210215 A1 | 9/2011 | Nitsche et al. |
| 2011/0251519 A1 | 10/2011 | Romoscanu |
| 2012/0065469 A1 | 3/2012 | Allyn et al. |
| 2012/0203058 A1 | 8/2012 | Kanapkey et al. |
| 2012/0259208 A1 | 10/2012 | Bloom et al. |
| 2012/0260921 A1 | 10/2012 | Sangwan |
| 2013/0006323 A1 | 1/2013 | Tal et al. |
| 2013/0197321 A1 | 8/2013 | Wilson |
| 2013/0282078 A1 | 10/2013 | Wacnik |
| 2014/0000622 A1 | 1/2014 | Azagury et al. |
| 2014/0012235 A1 | 1/2014 | Pinchuk et al. |
| 2014/0128936 A1 | 5/2014 | Laufer et al. |
| 2014/0276663 A1 | 9/2014 | Pinchuk et al. |
| 2014/0288382 A1 | 9/2014 | Lemmens et al. |
| 2014/0288384 A1 | 9/2014 | Mulrooney |
| 2014/0303617 A1 | 10/2014 | Shimada |
| 2014/0378941 A1 | 12/2014 | Su et al. |
| 2015/0224280 A1 | 8/2015 | Pinchuk et al. |
| 2017/0050014 A1 | 2/2017 | Rizik |
| 2017/0224986 A1 | 8/2017 | Imran et al. |
| 2017/0312497 A1* | 11/2017 | Mulrooney .......... A61N 1/0519 |
| 2018/0214672 A1 | 8/2018 | Mulrooney |
| 2018/0235533 A1 | 8/2018 | Mulrooney |
| 2019/0038894 A1 | 2/2019 | Bassi et al. |
| 2019/0134380 A1 | 5/2019 | Mulrooney |
| 2019/0134389 A1 | 5/2019 | Mulrooney |
| 2020/0061369 A1 | 2/2020 | Mulrooney et al. |
| 2020/0061370 A1 | 2/2020 | Mulrooney et al. |
| 2020/0179045 A1 | 6/2020 | Levin et al. |
| 2020/0306528 A1 | 10/2020 | Linden et al. |
| 2020/0330025 A1 | 10/2020 | Mulrooney |
| 2021/0077784 A1 | 3/2021 | Mulrooney |
| 2021/0077808 A1 | 3/2021 | Mulrooney et al. |
| 2022/0160537 A1 | 5/2022 | Mulrooney |
| 2022/0161029 A1 | 5/2022 | Mulrooney |
| 2022/0161030 A1 | 5/2022 | Mulrooney |
| 2022/0313981 A1 | 10/2022 | Mulrooney |
| 2023/0181023 A1 | 6/2023 | Mulrooney |
| 2023/0302244 A1 | 9/2023 | Mulrooney |
| 2024/0009451 A1 | 1/2024 | Mulrooney |
| 2024/0299746 A1 | 9/2024 | Mulrooney |

FOREIGN PATENT DOCUMENTS

| | | |
|---|---|---|
| CN | 203954394 U | 11/2014 |
| CN | 204319485 U | 5/2015 |

(56) References Cited

FOREIGN PATENT DOCUMENTS

| EP | 0510857 A1 | 10/1992 |
|----|------------|---------|
| EP | 0571514 A1 | 12/1993 |
| EP | 1179307 A2 | 2/2002 |
| EP | 1047469 B1 | 6/2003 |
| EP | 2253350 A1 | 11/2010 |
| EP | 2693968 A1 | 2/2014 |
| EP | 2693968 B1 | 3/2016 |
| EP | 3331597 A1 | 6/2018 |
| GB | 2169206 A | 7/1986 |
| GB | 2254253 A | 10/1992 |
| GB | 2294642 A | 5/1996 |
| GB | 2313316 A | 11/1997 |
| GB | 2532044 A | 5/2016 |
| GB | 2541039 A | 2/2017 |
| JP | S63200771 A | 8/1988 |
| JP | H05115563 A | 5/1993 |
| JP | H07500523 A | 1/1995 |
| JP | H08505291 A | 6/1996 |
| JP | 2556694 B2 | 11/1996 |
| JP | H10118190 A | 5/1998 |
| JP | 2005312969 A | 11/2005 |
| JP | 2012512722 A | 6/2012 |
| JP | 2014068716 A | 4/2014 |
| WO | 9400050 A1 | 1/1994 |
| WO | 9405361 A1 | 3/1994 |
| WO | 9526777 A1 | 10/1995 |
| WO | 9715349 A1 | 5/1997 |
| WO | 9719667 A1 | 6/1997 |
| WO | 9844973 A1 | 10/1998 |
| WO | 03026741 A1 | 4/2003 |
| WO | 2005051472 A2 | 6/2005 |
| WO | 2006024825 A1 | 3/2006 |
| WO | 2007129002 A1 | 11/2007 |
| WO | 2009154718 A1 | 12/2009 |
| WO | 2010023579 A1 | 3/2010 |
| WO | 2010071812 A1 | 6/2010 |
| WO | 2010091440 A2 | 8/2010 |
| WO | 2012131303 A1 | 10/2012 |
| WO | 2013109835 A1 | 7/2013 |
| WO | 2014152808 A1 | 9/2014 |
| WO | 2015027094 A1 | 2/2015 |
| WO | 2017089752 A1 | 6/2017 |
| WO | 2020183325 A1 | 9/2020 |
| WO | 2022106843 A1 | 5/2022 |
| WO | 2022106844 A1 | 5/2022 |

OTHER PUBLICATIONS

Takeishi, et al., "Effects of Pharyngeal Electrical Stimulation on Swallowing Performance", PLOS One 13(1): e0190608. https://doi.org/10.1371/journal.pone.0190608 (Year: 2018).

Bath et al., Pharyngeal electrical stimulation for neurogenic dysphagia following stroke, traumatic brain injury or other causes: Main results from the PHADER cohort study, EClinical Medicine 28 (2020) 100608, 9 pages.

Bath et al., Pharyngeal Electrical Stimulation for Treatment of Dysphagia in Subacute Stroke A Randomized Controlled Trial, Stroke, Jun. 2016, vol. 47, Issue 6, pp. 1562-1570.

Dziewas et al., Design and implemental of Pharyngeal electrical Stimulation for early de-cannulation in TRACheotomized (PHAST-TRAC) stroke patients with neurogenic dysphagia, International Journal of Stroke, 12(4), 2017, pp. 430-437.

Dziewas et al., PHAryngeal electrical STimulation for early decannulation in TRACheotomised patients with neurogenic dysphagia after stroke (PHAST-TRAC): a prospective, single-blinded, randomised trial, Lancet Neurology, vol. 17, Issue 10, 2018, 29 pages.

Essa et al., The BDNF polymorphism VAL66Met may be predictive of swallowing improvement post pharyngeal electrical stimulation in dysphagic stroke patients, Neurogastroenterol Motil, 2017; 27, 7 pages.

European Patent Office, International Search Report and Written Opinion for International Application No. PCT/GB2021/053011, Feb. 24, 2022, 16 pages.

Fraser et al., Differential changes in human pharyngoesophageal motor excitability induced by swallowing, pharyngeal stimulation, and anesthesia, Am J Physiol Gastrointest Liver Physiol, 285: G-137-G144, 2003.

Hamdy et al., The cortical topography of human swallowing musculature in health and disease, Nature Medicine, vol. 2, No. 11, Nov. 1996, pp. 1217-1224.

Hamdy, et al., Long-term reorganization of human motor cortex driven by short-term sensory stimulation, Nature Neuroscience, vol. 1, No. 1, May 1998, pp. 64-68.

International Search Report and Written Opinion mailed May 12, 2022, International Application No. PCT/GB2021/053008, 21 pages.

Jayasekeran et al., Adjunctive Functional Pharyngeal Electrical Stimulation Reverses Swallowing Disability After Brain Lesions, Gastroenterology, 2010; vol. 138, No. 5, pp. 1737-1746.

Koestenberger, et al., A Pilot Study of Pharyngeal Electrical Stimulation of Orally Intubated ICU Patients with Dysphagia, Neurocrit Care (2020) 32: 532-538.

Magara et al., Tu1254 Does Combining Pharyngeal Electrical Stimulation With Simultaneous Swallowing of Carbonated Liquids Enhance the Cortical Swallowing Motor System?, Gastroenterology, Apr. 2016 [Abstract only].

Magara, et al., Exploring the effects of synchronous pharyngeal electrical stimulation with swallowing carbonated water on cortical excitability in the human pharyngeal motor system, Neurogastroenterol Motil (2016), 11 pages.

Restivo et al., Pharyngeal electrical stimulation device for the treatment of neurogenic dysphagia: technology update, Medical Devices: Evidence and Research, 2018: 11, pp. 21-26.

Restivo et al., Pharyngeal Electrical Stimulation for Dysphagia Associated with Multiple Sclerosis: A Pilot Study, Brain Stimulation 6, 2013, pp. 418-423.

Sasegbon et al., Advances in the Use of Neuromodulation for Neurogenic Dysphagia: . . . , American Journal of Speech-Language Pathology, Jul. 2020, vol. 29, pp. 1044-1064.

Scutt, et al., Pharyngeal Electrical Stimulation for Treatment of Poststroke Dysphagia: Individual Patient Data Meta-Analysis of Randomised Controlled Trials, Stroke Research and Treatment, 2015, 8 pages.

Suntrup et al., Electrical pharyngeal stimulation for dysphagia treatment in tracheotomized stroke patients: a randomized controlled trial, Intensive Care Med (2015) 41: 1629-1637.

Suntrup-Krueger et al., Electrical pharyngeal stimulation increases substance p. level in saliva, Neurogastroenterol Motil (2016) 28, pp. 855-860.

Vasant et al., Pharyngeal Electrical Stimulation in Dysphagia Poststroke: A Prospective, Randomized Single-Blinded Interventional Study, Neurorehabilitation and Neural Repair, 2016, vol. 30(9), pp. 866-875.

Fraser, Chris , et al., "Driving Plasticity in Human Adult Motor Cortex is Associated with Improved Motor Function After Brain Injury", Neuron, vol. 34, May 30, 2002, pp. 831-840.

Gow, David , et al., "Characterising the Central Mechanisms of Sensory Modulation in Human Swallowing Motor Cortex", Clinical Neurophysiology, Elsevier Science, IE, vol. 115, No. 10, Jun. 26, 2004, pp. 2382-2390.

Hamdy, S. , et al., "Modulation of human swallowing behaviour by thermal and chemical stimulation in health and after brain injury", Neurogastroenterol Motil, vol. 15, No. 1, Feb. 2003, pp. 69-77.

Hamdy, Shaheen , et al., "Recovery of Swallowing After Dysphagic Stroke Relates to Functional Reorganization in the Intact Motor Cortex", Gastroenterology, vol. 115, No. 5, Nov. 1998, pp. 1104-1112.

Kajii, Yuka , et al., "Sour taste stimulation facilitates reflex swallowing from the pharynx and larynx in the rat", Physiology & Behavior, vol. 77, No. 2-3, 2002, pp. 321-325.

Takeuchi, Hiro-Aki , et al., "Electrophysiological and Behavioral Studies of Taste Discrimination in the Axolotl (Ambystoma mexicanum)", Physiology & Behavior, vol. 56, No. 1, Jul. 1994, pp. 121-127.

Tutuian, R. , et al., "Effects of position on oesophageal function: studies using combined manometry and multichannel intraluminal impedance", Neurogastroenterol Motil., vol. 15, No. 1, Feb. 2003, pp. 63-67.

(56) References Cited

OTHER PUBLICATIONS

Wassermann, Eric M., "Risk and safety of repetitive transcranial magnetic stimulation: report and suggested guidelines from the International Workshop on the Safety of Repetitive Transcranial Magnetic Stimulation, Jun. 5-7, 1996", Electroencephalography and clinical Neurophysiology, vol. 108,, 1998, pp. 1-16.
Jasper, Herberth. , "The Ten Twenty Electrode System of the International Federation", Clinical Neurophysiol, vol. 10, 1957, pp. 370-375.

* cited by examiner

DEVICES, SYSTEMS, AND METHODS FOR TREATING DISEASE USING ELECTRICAL STIMULATION

CROSS REFERENCE TO RELATED APPLICATION

The present application is a 371 U.S. national phase application of International Application No. PCT/GB2021/ 053011, titled DEVICES, SYSTEMS, AND METHODS FOR TREATING DISEASE USING ELECTRICAL STIMULATION, filed Nov. 19 2021, which claims the benefit of priority to U.S. Provisional Application No. 63/198,881, filed Nov. 19, 2020, titled DEVICES, SYS- TEMS, AND METHODS FOR TREATING DISEASE USING ELECTRICAL STIMULATION, filed Nov. 19, 2020, each of which is incorporated by reference herein in its entirety.

TECHNICAL FIELD

The present disclosure is directed generally to devices, systems, and methods for treating disease using electrical stimulation. Particular embodiments include treating dysphagia by applying electrical stimulation to a target neural population of the patient.

BACKGROUND

Dysphagia is the condition whereby a patient has diffi- culty in swallowing or is unable to swallow safely. Dyspha- gia may be caused, for example, by stroke, neurodegenera- tive diseases, brain tumors or in some cases by other co-morbidities, such as respiratory disorders. It has been reported that between 7 and 10% of all adults older than 50 years of age present with clinically significant dysphagia. Of those over the age of 60, this increases to 14%. In total, 10 million Americans are evaluated each year in clinics and hospitals for swallowing difficulties. It has also been reported that over 51% of institutionalized elderly patients present with oropharyngeal dysphagia.

Swallowing is a rigidly ordered sequence of events that results in the propulsion of food from the mouth through the pharynx and esophagus to the stomach. At the same time, respiration is inhibited and food is prevented from entering into the trachea. Swallowing can be initiated voluntarily, but thereafter it is almost entirely under reflex control. The swallow reflex is typically initiated by sensory impulses from tactile receptors (particularly those located near the opening of the pharynx) being transmitted to certain areas in the medulla. The central integrating areas for swallowing lie in the medulla and lower pons; they are collectively called the swallowing center. Motor impulses travel from the swallowing center to the musculature of the pharynx and upper esophagus via various cranial nerves. This lower swallowing center in the brainstem is under regulatory control by higher center in the cerebral cortex. These higher swallowing centers or regions control the voluntary initia- tion and modulation of the swallow.

Swallowing occurs in three stages. In the oral or voluntary phase, food is moved towards the back of the mouth by the tongue, and forced into the pharynx, where it stimulates the tactile receptors that initiate the swallowing reflex. In the pharyngeal stage of swallowing, food passes through the pharynx by constriction of the walls of the pharynx, back- ward bending of the epiglottis, and an upward and forward movement of the larynx and trachea. During the pharyngeal stage, respiration is reflexively inhibited. In the esophageal stage of swallowing, food moves down the esophagus and into the stomach, assisted by one or more peristaltic waves.

Although the main function of swallowing is the propul- sion of food from the mouth into the stomach, swallowing also serves as a protective reflex for the upper respiratory tract, preventing unwanted particles from entering the tract. Food or liquid that enters into the airways may act as a locus for infection and this type of infection can be life threaten- ing. For instance, dysphagia after a stroke can be a devas- tating problem, as it carries a six-fold increased risk of aspiration pneumonia.

Complications that have been associated with dysphagia include pneumonia, malnutrition, dehydration, poorer long- term outcome, increased length of hospital stay, increased rehabilitation time and the need for long-term care assis- tance, increased mortality, and increased health care costs. These complications impact the physical and social wellbe- ing of patients, quality of life of both patients and caregivers, and the utilization of health care resources.

In view of the above, there remains a need for improved devices and methods that can treat dysphagia.

SUMMARY

The present technology relates to electrical stimulation devices and associated systems and methods. In particular embodiments, the present technology comprises electrical stimulation devices configured to perform pharyngeal elec- trical stimulation (PES) to treat one or more conditions. Several embodiments of the present disclosure, for example, are configured to perform PES to treat a patient suffering from neurogenic dysphagia. Electrical stimulation of nerves proximate the patient's pharynx increases activity in the motor cortex and other areas of the brain to facilitate a functional reorganization of the centers in the brain respon- sible for controlling and coordinating swallow function. The subject technology is illustrated, for example, according to various aspects described below, including with reference to FIGS. 1-5C. Various examples of aspects of the subject technology are described as numbered clauses (1, 2, 3, etc.) for convenience. These are provided as examples and do not limit the subject technology.

1. A device comprising:
   an elongated member for nasal insertion into a patient's pharynx, the elongated member having a proximal portion, a distal portion, and a longitudinal axis, wherein the elongated member comprises a first region having a first stiffness and a second region proximal of the first region along the longitudinal axis, and wherein the second region has a second stiffness less than the first stiffness; and
   a conductive element carried by the distal portion of the elongated member and configured to be electrically coupled to an energy source for delivering electric current to nerves proximate the pharynx,
   wherein, when the elongated member is inserted through a nostril of the patient such that the distal portion is positioned at a treatment site within the pharynx, the conductive element is placed in appo- sition with the pharyngeal wall, the first region extends along at least a portion of the nasal cavity and at least a portion of the nasopharynx, and the second region is positioned at or proximal of the patient's nostril.
2. The device of Clause 1, wherein the elongated member further comprises a third region distal of the first region along the longitudinal axis of the elongated member, and wherein the third region has a stiffness different than the stiffness of the first region.

3. The device of Clause 1 or Clause 2, further comprising a distal element at the distal portion of the elongated member and positioned distal to the first region, wherein the distal element has a curved distal end portion configured to guide the distal portion of the elongated member around the nasopharynx and into the oropharynx during insertion of the device through the nasal cavity.

4. The device of any one of Clauses 1 to 3, wherein the conductive element is positioned along the first region of the elongated member.

5. The device of any one of Clauses 1 to 4, wherein a sidewall of the elongated member comprises a structural member coextensive with the first and second regions, wherein the structural member is at least one of a coil or a braid.

6. The device of any one of Clauses 1 to 4, wherein the device further comprises a structural member disposed within a lumen of the elongated member, wherein the structural member is at least one of a coil or a braid.

7. The device of Clause 5 or Clause 6, wherein the structural member comprises a coil having a first length with a first pitch and a second length with a second pitch different than the first pitch.

8. The device of Clause 7, wherein the first length of the coil is coextensive with the first region of the shaft and the second length of the coil is coextensive with the second region of the shaft.

9. The device of Clause 5 or Clause 6, wherein the structural member comprises a braid having a variable stiffness along its length.

10. The device of any one of Clauses 1 to 9, wherein the first region of the elongated member is configured to be positioned proximal to an upper esophageal sphincter of the patient when the conductive element is delivering electric current to the nerves.

11. The device of any one of Clauses 1 to 10, wherein the elongated member has a closed distal end.

12. The device of any one of Clauses 1 to 11, wherein the electric current delivered to the nerves proximate the pharynx is configured to treat dysphagia.

13. A device comprising:

an elongated member for nasal insertion into a patient's pharynx, the elongated member having a proximal portion, a distal portion, a biasing region between the proximal and distal portions, and a longitudinal axis, wherein the elongated member has a variable stiffness along the longitudinal axis; and a conductive element carried by the distal portion of the elongated member and configured to be electrically coupled to an energy source for delivering electric current to nerves proximate the pharynx, wherein the biasing region is biased towards a straight configuration such that, when the elongated member is inserted through a nostril of the patient and the biasing region bends around the nasopharyngeal junction, the elongated member applies a restoring force that holds the conductive element in contact with a posterior region of the pharyngeal wall.

14. The device of Clause 13, wherein a stiffness of the elongated member along the biasing region is greater than a stiffness of a portion of the elongated member proximal of the biasing region.

15. The device of Clause 14, wherein the portion of the elongated member is configured to be positioned at or proximal of the patient's nostril when the elongated member is positioned within the pharynx and delivering electric current.

16. The device of any one of Clauses 13 to 15, further comprising a distal element at the distal portion of the elongated member and positioned distal to the second region, wherein the distal element has a curved distal end portion configured to guide the distal portion of the elongated member around the nasopharynx and into the oropharynx during insertion of the device through the nasal cavity.

17. The device of any one of Clauses 13 to 16, wherein the conductive element is positioned along the biasing region of the elongated member.

18. The device of any one of Clauses 13 to 17, wherein a sidewall of the elongated member comprises a structural member coextensive with the biasing region, wherein the structural member is at least one of a coil or a braid.

19. The device of any one of Clauses 13 to 18, wherein the distal portion of the elongated member is configured to be positioned proximal to an upper esophageal sphincter of the patient when the conductive element is delivering electric current to the nerves.

20. The device of any one of Clauses 13 to 19, wherein the elongated member has a closed distal end.

21. The device of any one of Clauses 13 to 20, wherein the electric current delivered to the nerves proximate the pharynx is configured to improve a swallowing reflex of the patient.

22. A method comprising:

inserting an elongated member through a nostril of a patient, the elongated member comprising a first region having a first stiffness and a second region having a second stiffness less than the first stiffness;

advancing the elongated member through the nasal cavity and into the pharynx such that a distal portion of the elongated member is positioned in the pharynx, wherein, when the distal portion is positioned in the pharynx, the first region spans a nasopharyngeal junction and the second region is positioned at or proximal of the patient's nostril; and stimulating nerves proximate the treatment site via a conductive element carried by the distal portion of the elongated member.

23. The method of Clause 22, further comprising urging the conductive element into contact with a posterior wall of the pharynx via a restoring force provided by the first region.

24. The method of Clause 22 or Clause 23, wherein the distal portion of the elongated member does not extent distally through the upper esophageal sphincter.

25. The method of any one of Clauses 22 to 24, wherein stimulation of the nerves proximate the treatment site improves a swallowing reflex of the patient.

26. A device comprising:

an elongated member for nasal insertion into a patient's pharynx, the elongated member having a proximal portion, a distal portion, and a longitudinal axis, wherein the elongated member comprises a first region having a first stiffness and a second region proximal of the first region along the longitudinal axis, and wherein the second region has a second stiffness less than the first stiffness; and a conductive element carried by the distal portion of the elongated member and configured to be electrically coupled to an energy source for delivering electric current to nerves proximate the pharynx; and a distal element at the distal portion of the elongated member, wherein the distal element has a curved distal end portion configured to guide the distal portion of the elongated member around the nasopharynx and into the oropharynx during insertion of the device through the nasal cavity, wherein, when the elongated member is inserted through a nostril of the patient such that the distal portion is positioned at a treatment site within the pharynx, the conductive element is placed in apposition with the pharyngeal wall.

27. A device comprising:

an elongated member for oral insertion into a patient's pharynx, the elongated member having a proximal portion, a distal portion, and a longitudinal axis, wherein the elongated member comprises a first region having a first stiffness and a second region proximal of the first region along the longitudinal axis, and wherein the second region has a second stiffness less than the first stiffness; and a conductive element carried by the distal portion of the elongated member and configured to be electrically coupled to an energy source for delivering electric current to nerves proximate the pharynx; and a distal element at the distal portion of the elongated member, wherein the distal element has a curved distal end portion configured to guide the distal portion of the elongated member around the base of the tongue and into the oropharynx during insertion of the device through the oral cavity, wherein, when the elongated member is inserted through a mouth of the patient such that the distal portion is positioned at a treatment site within the pharynx, the conductive element is placed in apposition with the pharyngeal wall.

28. A device comprising:

an elongated member for oral insertion into a patient's pharynx, the elongated member having a proximal portion, a distal portion, and a longitudinal axis, wherein the elongated member comprises a first region having a first stiffness and a second region proximal of the first region along the longitudinal axis, and wherein the second region has a second stiffness less than the first stiffness; and a conductive element carried by the distal portion of the elongated member and configured to be electrically coupled to an energy source for delivering electric current to nerves proximate the pharynx, wherein, when the elongated member is inserted through a mouth of the patient such that the distal portion is positioned at a treatment site within the pharynx, the conductive element is placed in apposition with the pharyngeal wall, the first region extends along at least a portion of the oral cavity and at least a portion of the oropharynx, and the second region is positioned at or proximal of the patient's mouth.

29. The device of Clause 28, wherein the elongated member further comprises a third region distal of the first region along the longitudinal axis of the elongated member, and wherein the third region has a stiffness different than the stiffness of the first region.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

As previously mentioned, the present technology comprises electrical stimulation devices configured to perform PES to treat one or more conditions. Conventional PES devices comprise a stimulation catheter and a feeding tube slidably positioned through a lumen of the stimulation catheter. PES to treat dysphagia is currently performed on patients already hospitalized, usually for the condition or trauma causing the dysphagia (e.g., acute stroke, traumatic brain injury, oral intubation, tracheotomy, etc.). In these cases, a single device is inserted into the patient and left in place for the entire treatment regimen, which can last up to six days. However, many patients suffering from dysphagia, such as long term chronic dysphagia patients, do not require hospitalization. Rather, these patients are better suited for treatment in an outpatient or community setting in which a multi-day catheter placement is not a practical option. To address the foregoing challenges, the devices and systems disclosed herein are configured for use without a feeding tube and can be used for single-use treatments.

To compensate for the loss of anatomical posturing previously provided by the feeding tube, the devices of the present technology advantageously include a positional and directional bias. By way of background, when a PES device comprising a stimulation catheter and feeding tube is positioned for treatment, the feeding tube (and sometimes the stimulation catheter) necessarily extends through the upper esophageal sphincter (UES) en route to the stomach. The engagement between the feeding tube and the UES biases the distal portion of the PES device towards the posterior wall and in so doing ensures good contact between the electrodes at the distal portion and the posterior wall (where the targeted nerves lie). Without the feeding tube to help anchor the stimulation catheter's position via engagement with the UES, the stimulation catheter tends to be biased towards the anterior portion of the pharynx (such as the epiglottis and airways) by virtue of passing through the curve of the nasopharynx. This is especially true as it relates to shorter catheters that do not pass through the UES and that have electrodes at or near the distal end (thus creating a stiffer region). To counteract this tendency, the devices and systems of the present technology include an elongated member with a positional and directional bias that leverages the nasopharyngeal anatomy to encourage proper positioning of the stimulation electrodes and contact with the posterior pharyngeal wall, as detailed herein.

Figure 1A:
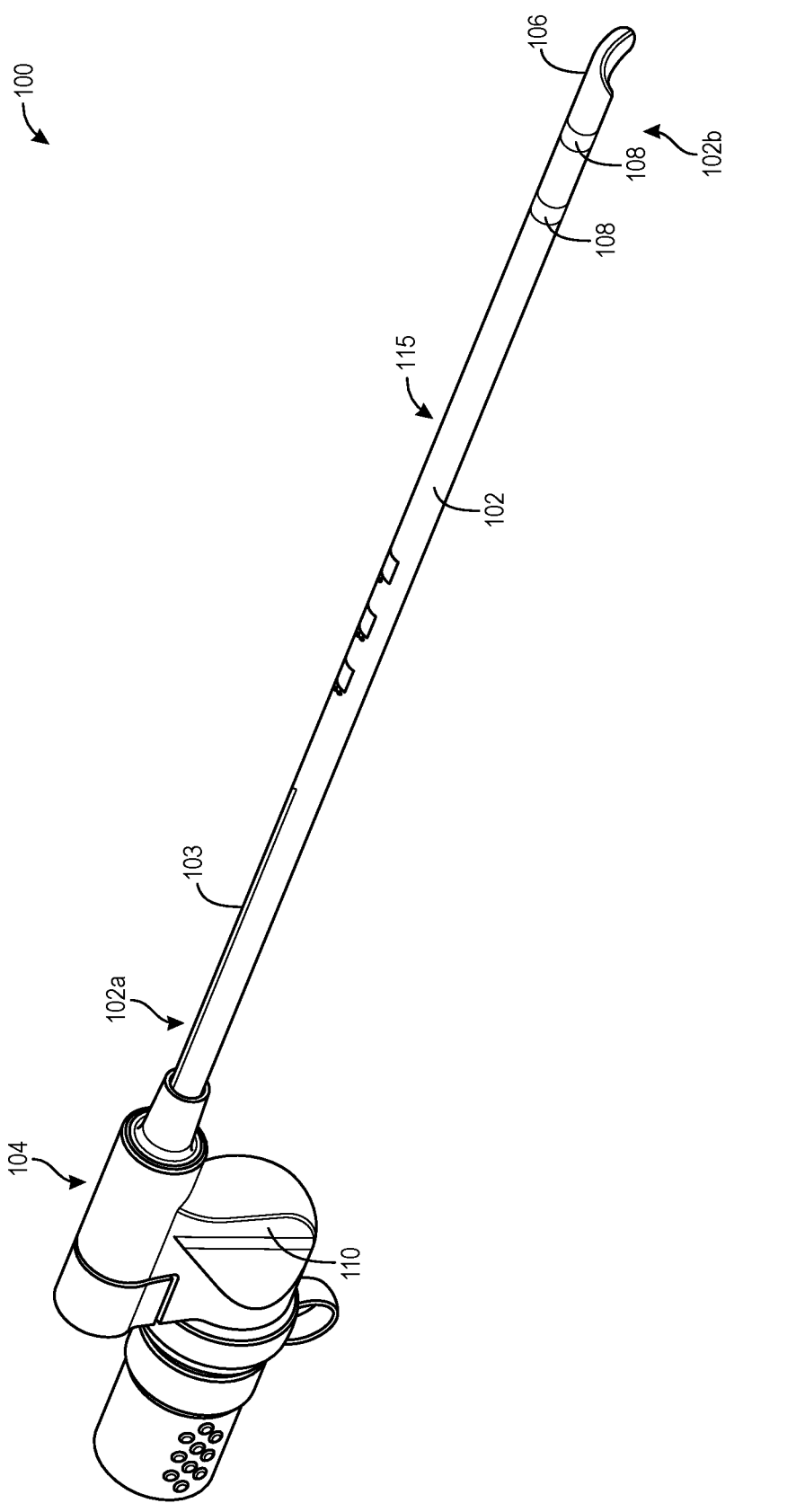
FIG. 1A depicts an electrical stimulation device in accordance with several embodiments of the present technology.

FIG. 1A depicts a device 100 ("device 100") of the present technology configured to provide intraluminal electrical pharyngeal neuromuscular stimulation to a patient suffering from dysphagia. As shown in FIG. 1A, the device 100 can include a handle assembly 104 and an elongated member 102 (or "member 102") having a proximal portion 102*a* coupled to the handle assembly 104 and a distal portion 102*b* configured to be positioned at a treatment site within a body lumen of a patient, such as within a portion of the patient's upper gastrointestinal tract. In some embodiments, the device 100 includes an atraumatic tip at the distal terminus of the elongated member 102. The device 100 further includes a pair of conductive elements 108 carried by the distal portion 102*b* of the member 102 and configured to deliver stimulation energy to nerves proximate the treatment site. In some embodiments, the handle assembly 104 includes a connector 110 for electrically coupling the device 100 to a current generator (not shown) configured to provide stimulation energy to the conductive elements 108. As described in greater detail herein, in some embodiments the elongated member 102 includes one or more biasing regions 115 configured to urge the conductive elements 108 towards the posterior pharyngeal wall in response to bends in the anatomy along the insertion path of the device 100.

As previously mentioned, the proximal portion of the device 100 and/or elongated member 102 can be configured to be electrically coupled to a current generator (not shown) for delivering electric current to the conductive elements 108. The current generator, for example, can include a power source and a controller. The controller includes a processor coupled to a memory that stores instructions (e.g., in the form of software, code or program instructions executable by the processor or controller) for causing the power source to deliver electric current according to certain parameters provided by the software, code, etc. The power source of the current generator may include a direct current power supply, an alternating current power supply, and/or a power supply switchable between a direct current and an alternating current. The current generator can include a suitable controller that can be used to control various parameters of the energy output by the power source or generator, such as intensity, amplitude, duration, frequency, duty cycle, and polarity.

The current generator may be configured to provide a stimulation energy to the conductive elements 108 that has an intensity, amplitude, duration, frequency, duty cycle, and/or polarity such that the conductive elements 108 apply an electric field at the treatment site that promotes neuroplasticity in the areas of the brain associated with swallowing control. The applied stimulus induces and accelerates a cortical reorganization process whereby responsibility for the control and coordination of swallowing activity is moved from the damaged area of the brain to a complementary area of the cortical centers with intact function. The applied stimulus also increases local levels of swallow-related neurotransmitters in the oropharynx. The current generator can provide, for example, a current of about 1 mA to about 50 mA, about 1 mA to about 40 mA, about 1 mA to about 30 mA, about 1 mA to about 20 mA, or about 1 mA to about 10 mA, at a frequency of about 1 Hz to about 50 Hz, about 1 Hz to about 40 Hz, about 1 Hz to about 30 Hz, about 1 Hz to about 20 Hz, about 1 Hz to about 10 Hz, about 2 Hz to about 8 Hz, about 1 Hz, about 2 Hz, about 3 Hz, about 4 Hz, about 5 Hz, about 6 Hz, about 7 Hz, about 8 Hz, about 9 Hz, or about 10 Hz, and having a pulse width of about 150 μS to about 250 μS, about 175 μS to about 225 μS, or about 200 μS.

Instead of or in addition to a controller, the current generator can include drive circuitry. In such embodiments, the current generator can include hardwired circuit elements to provide the desired waveform delivery rather than a software-based generator. The drive circuitry can include, for example, analog circuit elements (e.g., resistors, diodes, switches, etc.) that are configured to cause the power source to deliver electric current according to the desired parameters. For example, the drive circuitry can be configured to cause the power source to deliver periodic waveforms. In some embodiments, the drive circuitry can be configured to cause the power source to deliver a unipolar square wave.

Each of the conductive elements 108 may comprise an electrode, an exposed portion of a conductive material, a printed conductive material, and other suitable forms. In some embodiments, for example as shown in FIG. 1A, the conductive elements 108 comprise a pair of ring electrodes configured to be utilized in a bipolar fashion. The conductive elements 108 can be crimped, welded, or otherwise adhered to an outer surface of the elongated member 102. In some embodiments, the conductive elements 108 comprise a flexible conductive material disposed on the elongated member 102 via printing, thin film deposition, or other suitable techniques. While the device 100 shown in FIG. 1A includes two conductive elements 108, in some embodiments the device 100 may include more or fewer than two conductive elements 108. For example, the device 100 may comprise a single conductive element 108 configured to generate a monopolar electric field. Such embodiments include a neutral or dispersive electrode electrically connected to the current generator 120 and positioned on the patient's skin. In some embodiments, the device 100 may include three or more conductive elements 108 spaced apart along a longitudinal axis of the elongated member 102.

The device 100 may include one or more conductive leads (not shown) extending between a proximal portion of the device 100 and the conductive elements 108. In some embodiments, for example, the conductive leads comprise two wires extending between and electrically coupling the connector 110 and a corresponding one of the conductive elements 108. In some embodiments, the elongated member 102 includes a channel within and along which the conductive leads extend. The conducting leads can be insulated along all or a portion of their respective lengths.

As previously mentioned, the elongated member 102 includes one or more biasing regions 115 (one, some, or all of zone 114, zone 116, zone 118, and distal tip 106, discussed below) that predispose the elongated member 102 towards a desired insertion path that positions the conductive elements 108 at an optimal location for stimulation. To help the user maintain the rotational orientation of the elongated member 102 (and thus ensure that the directional bias provided by one or more biasing regions is acting in the desired direction), the elongated member 102 can include one or more indicators 103 along its length. The indicator 103 is configured to provide visual confirmation of the elongated member's orientation and can comprise one or more shapes, colors, symbols, numbers, letters, etc. The indicator 103 can be positioned at a proximal portion of the elongated member 102 such that at least a portion of the indicator 103 remains visible (i.e., outside of the patient) even once the device 100 is inserted into the patient.

The indicator 103 can also be disposed at a particular circumferential location that denotes a particular side of the elongated member 102 when the elongated member 102 is oriented correctly within the patient. For example, as shown in FIG. 1A, the indicator 103 can be disposed at a top side of the elongated member 102, which signals to the clinician that the indicator 103 should remain at the top side of the elongated member 102 during treatment to optimally leverage the preferential bending properties of the elongated member 102 and/or tip 106.

Although only a single indicator 103 is shown in FIG. 1A, the devices 100 of the present technology can include multiple indicators 103. The multiple indicators 103 can be at the same or different circumferential locations and at the same or different axial locations. In any of the embodiments disclosed herein, the indicators can communicate which side of the elongated member 102 they are intended to mark (e.g., "top," "right", "left," "bottom," etc.) The indicators 130 can have the same or different shape, size, color, etc. Moreover, although the indicator 103 shown in FIG. 1A comprises a continuous, axially-extending stripe along the outer surface of the elongated member 102, in In some embodiments, the systems of the present technology can include a separate temporary dressing applied to the nose that is configured to grip and prevent the elongated member from rotating). This ensures the orientation of the elongated member remains substantially unchanged.

As shown in FIG. 1A, the device 100 can include an atraumatic, closed distal tip 106 at the distal terminus of the elongated member 102. The distal tip 106 can have a rounded end for patient comfort and for ease of insertion of the elongated member 102 into the patient. For similar reasons, in some embodiments the tip 106 comprises a flexible and/or soft material. In some embodiments, the tip 106 can have a curved shape that directs the elongated member 102 downwardly (i.e., in an inferior direction) when the tip 106 meets the resistance of the posterior wall of the nasal cavity during insertion. The shape may include, for example, a crescent or partial C-shape. It will be appreciated that the tip 106 can have other suitable shapes and sizes.

Figure 1B:
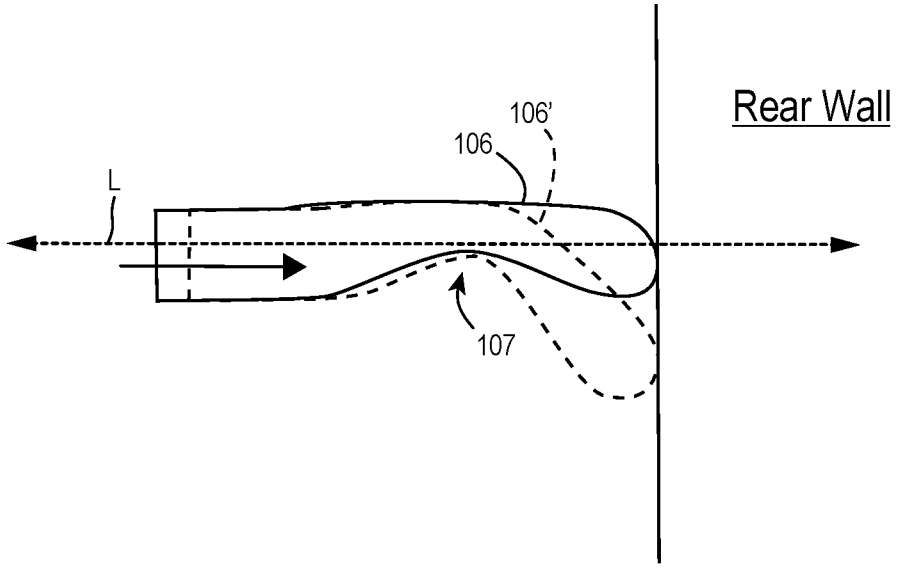
FIG. 1B shows a distal tip portion of the electrical stimulation device shown in FIG. 1A as it preferentially deflects downwardly when pushed against the posterior wall of the pharynx.

As depicted in FIG. 1B, the tip 106 can be directionally deformable such that it yields and/or changes shape when pressed against the rear wall of the nasal cavity, thereby bending along its longitudinal axis L and deflecting downwardly (e.g., in the direction of the pharynx). For example, the tip 106 can have a region that preferentially bends downwardly in response to an axially compressive force, thereby urging the elongated member 102 into a curved shape around the nasopharyngeal junction and reducing the amount of pressure needed to be applied by the operator. One of the most difficult aspects of inserting a prior art catheter and/or feeding tube into the pharynx through the nasal cavity is successfully passing through the bend at the rear of the nasal cavity. Often times the tip of the catheter can touch the back of the nasal cavity and either does not deflect at all, deflects sideways, or deflects upwardly and coils around the nasal cavity.

The shape of the tip 106 can be configured to encourage such preferential bending. For example, the tip 106 can have a bending region 107 along which the tip 106 is concave and/or narrowed such that the tip 106 preferentially bends at the bending region 107 when subjected to axially compressive forces. Additionally or alternatively, the bending region 107 can be formed of a portion of the tip 106 comprising a softer and/or more flexible material than other portions of the tip 106.

Optionally, the tip 106 may comprise a lubricious material (such as a lubricious coating) to facilitate movement of the elongated member 102 move into the pharynx. In some embodiments, the distal tip 106 may be a separate component that is fixedly coupled to the elongated member 102 during manufacturing. In some embodiments, the distal tip 106 is integral with the elongated member 102 (e.g., an extension of the tubular member forming the body of the elongated member 102). In yet other embodiments, the distal tip 106 is not configured to bend and/or preferentially bend.

Figure 2:
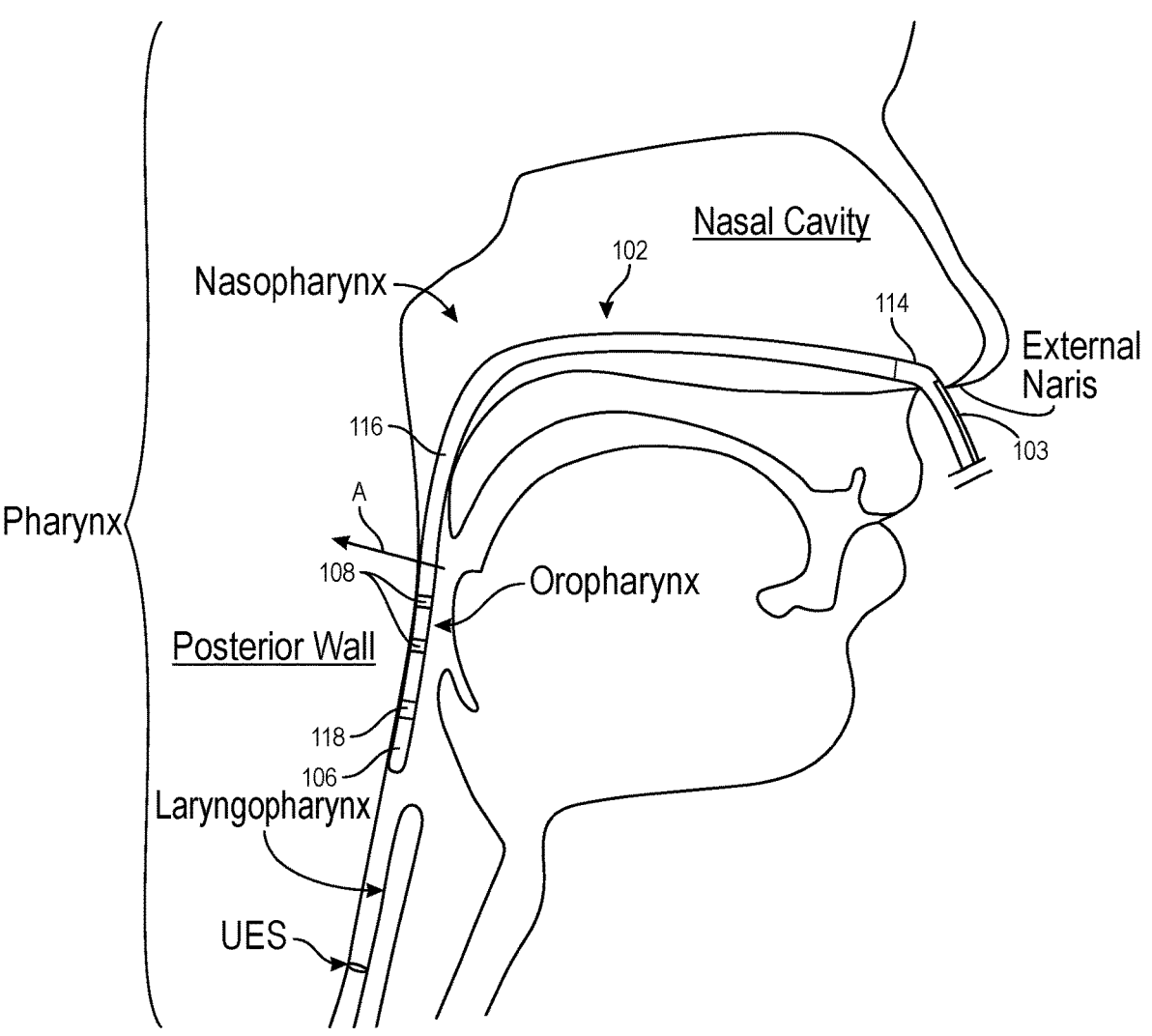
FIG. 2 depicts an electrical stimulation device transnasally inserted into a pharynx of a patient in accordance with several embodiments of the present technology.

FIG. 2 illustrates a fragmentary sagittal view of a patient with a device 100 of the present technology shown inserted through the patient's nasal cavity into the pharynx with the conductive elements 108 positioned in apposition with a posterior pharyngeal wall. In particular, the conductive elements 108 are positioned at the junction between the oropharynx and the laryngopharynx at a position that is equivalent to the junction between the C3 and C4 cervical vertebrae. In some embodiments, for example as shown in FIG. 2, the conductive elements 108 are bipolar electrodes spaced 10 mm apart along the longitudinal axis of the elongated member 102. In this position, the electrodes, or the electric field created by the electrodes, can flow through the posterior wall of the pharynx, base of the tongue, epiglottis, and areas above the larynx. Each of these regions include targeted nerves for treating dysphagia.

The density of sensory nerve supply to the oropharyngeal and laryngopharynx varies substantially. Without being bound by theory, the inventors believe that areas of higher density correspond to the reflexogenic areas that trigger pharyngeal swallowing and airway protection mechanisms. These high-density areas are the posterior wall of the pharynx (where the pharyngeal constrictor muscles are located), the posterior tonsillar pillar, the laryngeal surface of the epiglottis, and the postcricoid and arytenoid regions. The targeted sensory cranial nerves (CN) include: (a) The pharyngeal plexus, which is located on the pharyngeal constrictor muscles. The plexus is a network of nerve fibers formed from the pharyngeal branches of the glossopharyngeal (CN IX) and vagus (CN X) cranial nerves. (b) The superior laryngeal branch of the vagus nerve, which sends fibers to the lower epiglottis, and the lingual branch of the glossopharyngeal nerve, which sends fibers to the upper epiglottis. (c) The glossopharyngeal nerve, which is responsible for sensory innervation (taste and sensation) in the posterior areas of the tongue. (d) Sensory innervation to the glottis and laryngeal vestibule is by the internal branch of the superior laryngeal nerve. The external branch of the superior laryngeal nerve innervates the cricothyroid muscle. The superior laryngeal nerve is a branch of the vagus nerve (CN X).

As shown in FIG. 2, proper insertion of the device 100 requires the elongated member 102 to undergo at least two substantial bends. The first bend is at the junction between the nasal cavity and a location just proximal of the patient's nostrils. As the elongated member 102 extends proximally from the nostril, it may be beneficial for the elongated member 102 to bend downwardly (i.e., in an inferior direction) to facilitate attachment of the proximal portion of the device 100 (not shown) to the current generator. Additionally or alternatively, the elongated member 102 may bend medially or laterally immediately upon exiting the nostril to avoid extending over the patient's mouth. The elongated member 102 encounters the second bend, typically on the order of 90 degrees, when passing from the nasal cavity, through the nasopharynx, and into the oropharynx. This bend is sometimes referred to herein as the "nasopharyngeal junction."

Figure 3:
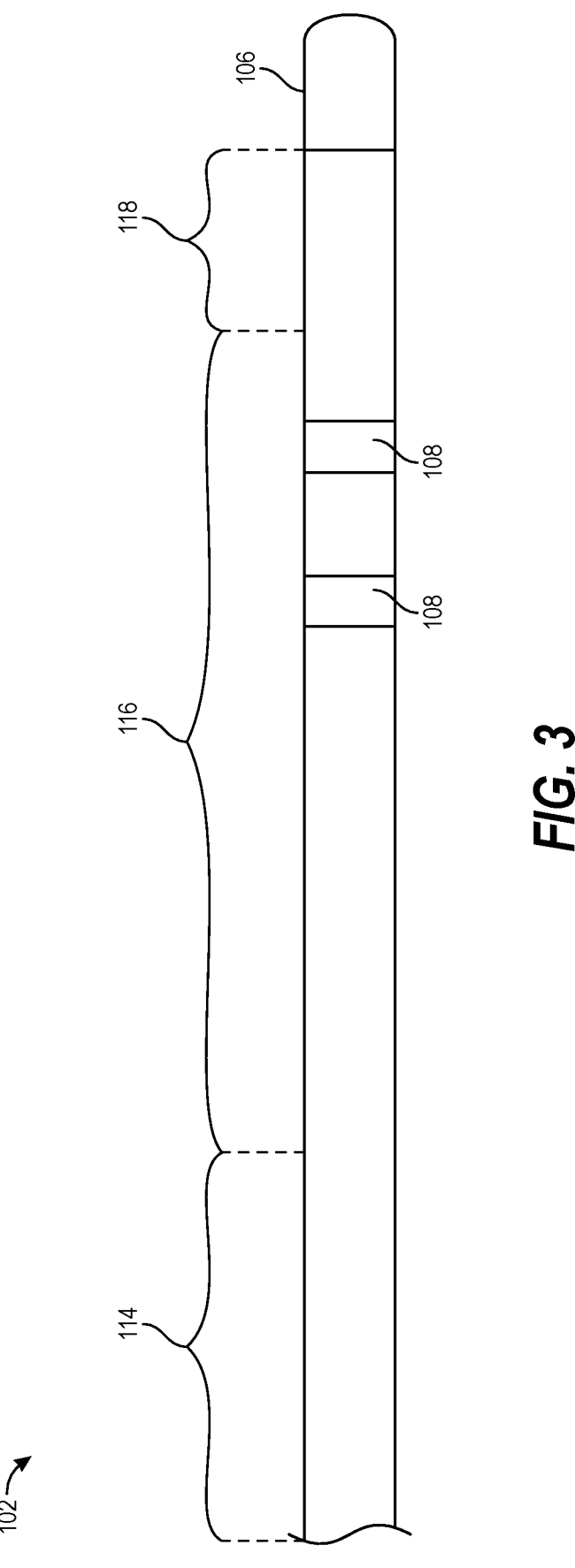
FIG. 3 is a cross-sectional schematic view of an elongated member of the electrical stimulation device shown in FIG. 1A.

Bearing in mind the foregoing anatomical and physiological considerations, the elongated member 102 can include a biasing region 115 configured to leverage the curvature of the native anatomy to anchor the conductive elements 108 in place against a posterior wall of the pharynx. The biasing region 115, for example, may be achieved by the inclusion of at least two different stiffness zones along the longitudinal axis of the elongated member 102. As shown in the enlarged side view of a portion of the elongated member 102 in FIG. 3, the elongated member 102 can have a first zone 114 having a first stiffness, a second zone 116 having a second stiffness, and a third zone 118 having a third stiffness. The first zone 114 may be proximal of the second zone 116, and the second zone 116 may be proximal of the third zone 118 along a longitudinal axis of the elongated member 102. In some embodiments, the elongated member 102 only includes the second and third zones 116, 118. In some embodiments, the elongated member 102 only includes the first and second zones 114, 116.

The different zones may have the same lengths or different lengths. According to certain embodiments, for example, a length of the second zone 116 is greater than a length of the first zone 114, which is greater than a length of the third zone 118. The lengths of each of the zones may depend, at least in part, on the anatomy along the insertion path. Although the following discussion is had with reference to an elongated member 102 for nasal insertion (and thus passing through the nasal cavity), the present technology also includes elongated members 102 for oral insertion (and thus passing through the oral cavity). For example, the elongated members 102 of the present technology configured to be inserted through the oral cavity can have a biasing region that accounts for the curvature of the insertion path between the base of the tongue and the pharynx.

When the device 100 is positioned in the patient's body with the conductive elements 108 at a treatment location, the first, more flexible zone 114 (relative to the second zone 116) can be positioned at or along the first bend at the nostril, thereby allowing the elongated member 102 to bend downwardly and/or medially or laterally, away from the nostril, for connection to the current generator. The second, stiffer zone 116 can be positioned at the nasopharyngeal junction such that a first, more proximal portion of the second zone 116 is at or proximal to the second bend, and a second, more distal portion of the second zone 116 is distal to the second bend and forced to bend downwardly into the pharynx. Because of the stiffness of the elongated member 102 along the second zone 116, the elongated member 102 is biased towards a straight position, and thus the elongated member 102 applies a posteriorly-directed force (indicated by arrow A) in an attempt to straighten out. In so doing, the elongated member 102 forces the conductive elements 108 into apposition with the posterior portion of the pharyngeal wall. Said another way, the second zone 116 acts like a spring and applies a restoring force to the pharynx when displaced by the second bend at the nasopharynx. In some embodiments, the elongated member 102 can also be secured externally to the patient to provide additional anchoring.

The third zone 118 of the elongated member may be positioned between the second zone 116 and the distal tip 106 and/or the distal terminus of the elongated member 102 and/or device 100. The third zone 118 may comprise a relatively short, flexible section that allows the flexible distal tip 106 to deflect downwardly when the tip 106 hits the posterior wall of the nasopharynx during insertion.

It is important to note that increasing the flexibility of a catheter shaft alone—without strategically located regions of varying flexibility that map to portions of the anatomy to be used as leverage points—will likely not result in the catheter being urged and/or biased against the posterior pharyngeal wall, at least when inserting the catheter through the nasal or oral cavity. For example, most extruded tubing tends to coil if left to its own devices. Additionally, when such tubing is passed through a curve (such as when passing through the nasopharynx), the portion of the tubing beyond the curve will not straighten out unless the operator acts on the tubing with a corrective force (such as a steering mechanism). Rather, beyond the curve, the tubing will just continue to curve. For catheters that pass through the UES, the catheter generally straightens out by virtue of it passing through the UES. For shorter catheters that do not have that interaction between the UES and the catheter, the catheter end will try to curve and head towards the entrance to the airways (i.e., the catheter will naturally be pushed away from the posterior wall of the pharynx). This is countered in some catheters by using a weighted end, but that solution only gets the catheter to point downwardly. The elongated member of the present technology, however, is configured to go even further and reverse the direction of the bend. For example, the internal spring force enabled by the unique design of the elongated member of the present technology can be advantageous for pushing the distal portion of the elongated member back towards the posterior wall. To this end, the device of the present technology can utilize certain portions of the anatomy, such as the nasopharynx or other portions, as a hinge/leverage point.

The varying stiffness of the elongated member 102 may be continuous or stepped by varying the size, shape, thickness, material composition, and/or structural components of the elongated member 102. For example, in some embodiments a sidewall of the elongated member 102 may have a thickness that varies to achieve a desired stiffness profile. According to several embodiments, portions of the sidewall of the elongated member may be selectively removed or skived to create regions of preferential bending. In some embodiments, the elongated member 102 includes a structural member that imparts a varying stiffness along the length of the elongated member 102. The stiffness profile, for example, may be tailored to the anatomy of the body lumen along the insertion path of the treatment device. The structural member can extend along the entire length of the elongated member 102 or substantially the entire length of the elongated member 102. In some embodiments, the structural member extends along only a portion of the length of the elongated member 102 (e.g., half the length of the elongated member 102 or less, one third the length of the elongated member 102 or less, etc.). The length of the structural member can vary depending upon, for example, the length of the elongated member 102 and the desired characteristics and functions of the device 100.

In some embodiments, the structural member comprises a coil integrated within the elongated member 102. The coil can be one or more round wires or flat ribbons helically wound around an inner portion of the elongated member 102. In some embodiments, a material comprising the sidewall of the elongated member 102 partially or completely encases the coil. The coil may have different zones of stiffness along its length. For example, the coil may have a first zone corresponding to the first zone 114 of the elongated member 102, a second zone corresponding to the second zone 116 of the elongated member 102, and a third zone corresponding to a third zone 118 of the elongated member. The first and third zones of the coil can be less stiff than the second zone. In some embodiments, the first zone of the coil has a first pitch, the second zone has a second pitch, and the third zone has a third pitch. The individual pitches of the first and third zones can be greater than the pitch of the second zone. In some embodiments, the coil only has two zones with different stiffnesses. In some embodiments, the coil has four or more zones with different stiffnesses.

The proximal terminus of the coil can be positioned along the distal portion of the elongated member 102, and the distal terminus of the coil can be positioned generally in alignment with or just proximal to the distal terminus of the elongated member 102. In some embodiments, at least a portion of the coil is outside of the distal portion of the elongated member 102. In some embodiments, the coil extends along the entire length of the elongated member 102 between the handle assembly 104 and the distal tip 106. The pitch of adjacent turns of the coil may be tightly wound so that each turn touches the succeeding turn or the pitch may be set such that the coil is wound in an open fashion. The pitch of the coil can be the same or may vary along the length of the coil.

The wire of the coil can comprise one or more metals, such as stainless steel, platinum, silver, tantalum, and the like. In other embodiments, the wire of the coil can include or be made of non-metallic materials. In a particular embodiment, the wires may comprise a superelastic, resilient, and/or shape-memory material, such as nitinol, a cobalt chromium alloy, or others. Additionally or alternatively, in some embodiments the coil can comprise a radiopaque or imaging material. In some embodiments, the coil is further shaped using a heat treatment process.

In some embodiments, the structural member comprises a tubular braid integrated within the elongated member 102. The braid can have a generally uniform pitch along its respective length or may have a varying pitch along its respective length. The flexibility of the braid may vary continuously along its respective length by continuously varying the pitch or may vary along its respective length in a stepwise fashion by stepwise varying the pitch. Moreover, the braid can have a generally constant braid angle along its respective length or have a varying braid angle along its respective length to provide different zones of stiffness and/or flexibility. The braid can be formed of braided filaments having the same or different diameters. In some embodiments, the braid is further shaped using a heat treatment process.

As previously mentioned, the braid may have different zones of stiffness along its length. For example, the braid may have a first zone corresponding to the first zone 114 of the elongated member 102, a second zone corresponding to the second zone 116 of the elongated member 102, and a third zone corresponding to a third zone 118 of the elongated member. The first and third zones of the braid can be less stiff than the second zone. In some embodiments, the first zone of the coil has a first pitch, the second zone has a second pitch, and the third zone has a third pitch. The individual pitches of the first and third zones can be greater than the pitch of the second zone. In some embodiments, the braid only has two zones having different stiffnesses. In some embodiments, the braid has four or more zones having different stiffnesses.

The wires forming the braid can comprise one or more metals, such as stainless steel, platinum, silver, tantalum, and the like. In other embodiments, the wire of the coil can include or be made of non-metallic materials. In a particular embodiment, the wires may comprise a superelastic, resilient, and/or shape-memory material, such as nitinol, a cobalt chromium alloy, others. Additionally or alternatively, in some embodiments the wires forming the braid comprise a radiopaque or imaging material.

In some embodiments, the structural member comprises a plurality of coils. In some embodiments, the structural member comprises a plurality of braids. In some embodiments, the structural member comprises a braid and multiple coils, a coil and multiple braids, or multiple braids and multiple coils. In those embodiments where the structural member comprises more than one sub-component, the sub-components may be arranged coaxially or end-to-end.

In some embodiments, the stiffness of the elongated member 102 decreases in a proximal to distal direction along its length in a continuous or step-wise fashion. In some embodiments, the stiffness of the elongated member 102 increases in a proximal to distal direction along its length in a continuous or step-wise fashion, and/or increases and decreases in a proximal to distal direction along its length in a continuous or step-wise fashion.

In some embodiments, the elongated member 102 defines a lumen extending at least partially therethrough. For example, the elongated member 102 may comprise a lumen extending from the proximal portion of the elongated member 102 to the closed distal tip 106. In some embodiments, the elongated member 102 has an opening at its distal terminus such that the lumen extends completely through the elongated member 102. In such embodiments, lumen is configured to slidably receive and facilitate the passage therethrough of one or more medical devices, such as a guidewire, a feeding tube, and others. In some embodiments, the lumen is configured to receive nutrients therethrough, and/or one or more fluids, such as radiopaque dye, saline, drugs, and the like.

The elongated member 102 can be constructed from two distinct layers, each comprising a different material. The first layer, for example, can be formed from fluorinated ethylene propylene and the second, outer layer can be formed from polyurethane. A pair of ring electrodes can be crimped to the external wall of the elongated member 102. The electrodes can be approximately 3 mm wide, positioned approximately 10 mm apart, and can be formed from medical grade stainless steel or platinum. Two wires can extend from the electrodes (or other conductive elements) and are received in separate lumens in the outer layer of the elongated member 102. The wires can be connected to the connector 110 which can provide the electrical interface between the device 100 and the current generator. In other embodiments, the elongated member 102 comprises other materials and/or configurations.

Any of the elongated members disclosed herein may be formed of a flexible material such as a thermoplastic elastomer (e.g., Pebax®), polyurethane, or another material suitable for forming devices. In some embodiments, the elongated member comprises a transparent material and/or includes one or more transparent portions. In some embodiments, the elongated member is formed of multiple layers of material. For example, the elongated member can comprise an outer layer of a flexible material (e.g., polyurethane) and an inner layer of a material with a low coefficient of friction and/or high dielectric strength (e.g., fluorinated ethylene propylene). An elongated member of the present technology may comprise a structure such as, but not limited to, a wire, a coil, or a braid, within a sidewall of the elongated member for reinforcement and/or kink-resistance.

In some embodiments, the elongated member 102 can be made of or include a radiopaque material for radiographic visualization. Exemplary radiopaque materials include, for example, gold, iridium, platinum, palladium, tantalum, tungsten alloy, polymer materials loaded with radiopaque fillers, and the like. Likewise, in some embodiments, the elongated member 102 comprises a material that may aid in MRI imaging, such as, for example, tungsten, Elgiloy, MP35N, nitinol, and others.

Figure 4:
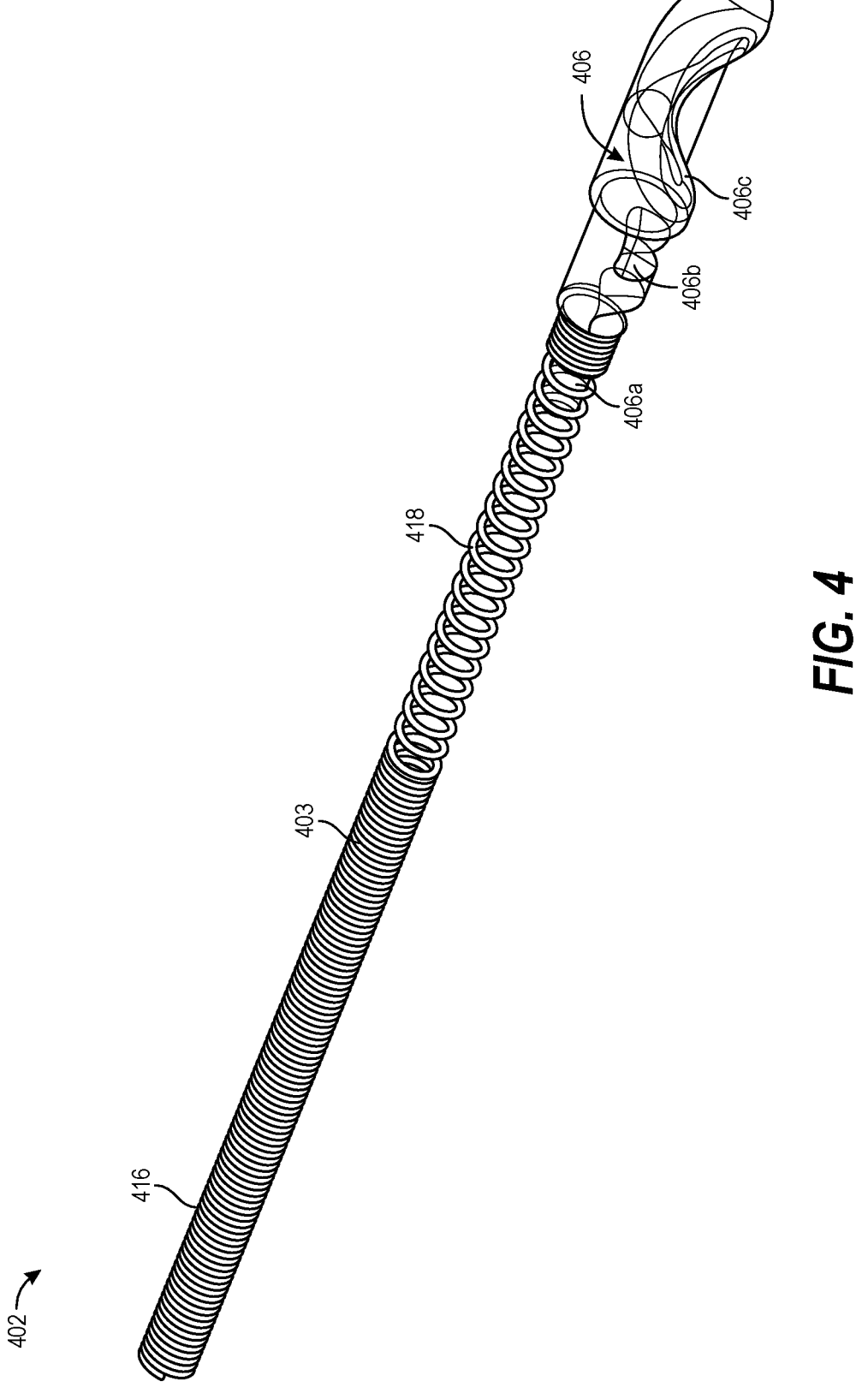
FIG. 4 is an isometric view of several components of an elongated member configured in accordance with several embodiments of the present technology.
Figures 5A, 5B, 5C:
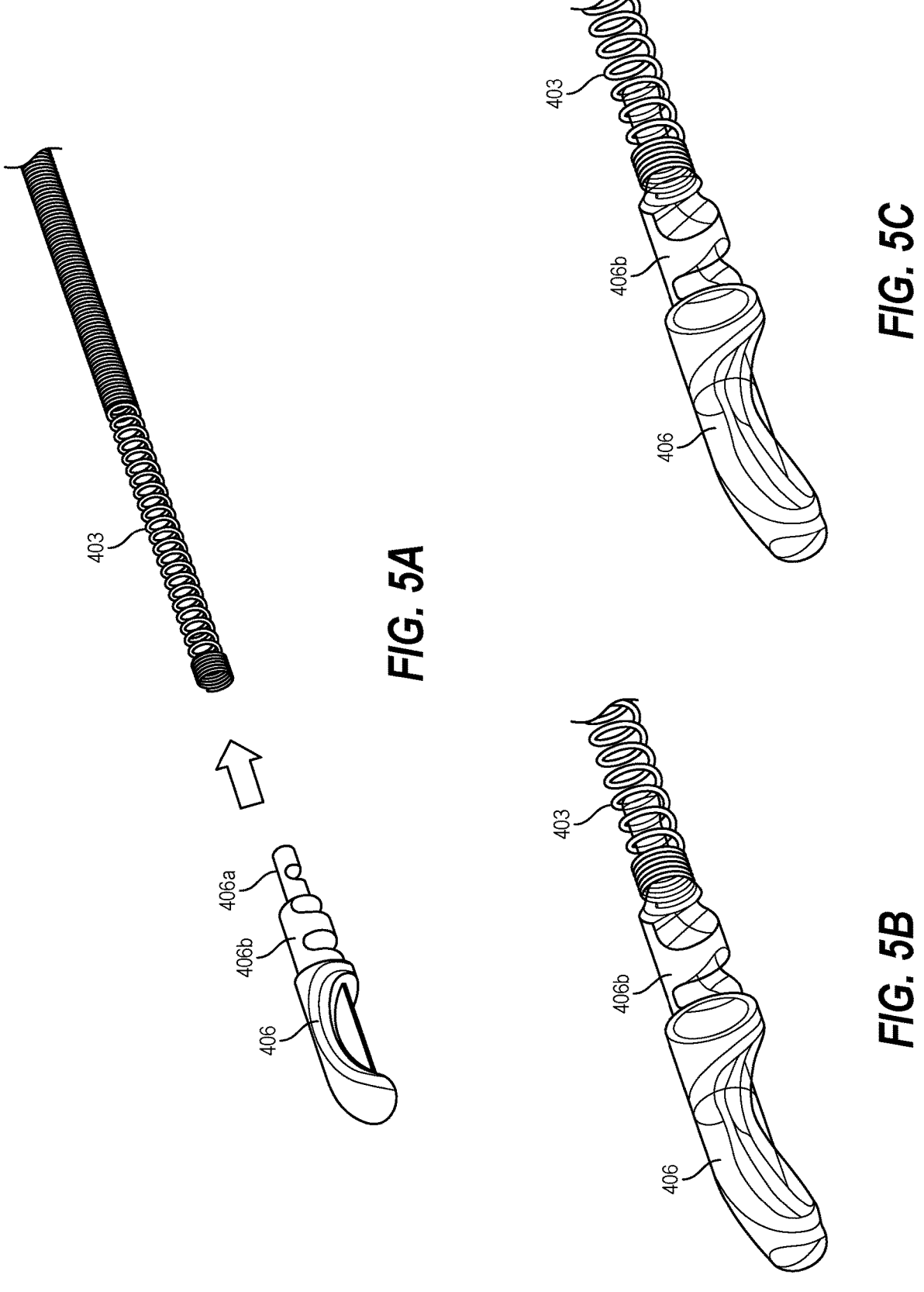
FIGS. 5A-5C depict a method for assembling several components of the elongated member shown in FIG. 4.

FIG. 4 is a perspective view of one example of an elongated member 402 of the present technology that includes a structural member 403. FIG. 4 shows only a distal portion of the elongated member 402, and the sidewall of the elongated member 402 has been removed for ease of viewing the structural member 403. As shown, the structural member 403 may comprise a coil, such as any of the coils disclosed herein. The coil may comprise a proximal region 416 having a tighter pitch, and a proximal region 418 having a wider pitch. As such, the proximal region 416 is stiffer then the distal region 418. As shown in FIGS. 5A-5C, in some example methods of making the elongated member, a narrow, proximal extension 406a of the distal tip 406 can be inserted into a distal end region of the coil such that a distal end of the coil abuts a shoulder between an intermediate portion 406b of the tip 406 and the curved, main body of the tip. A securing member may then be crimped around the distal end region of the coil and the proximal extension 406a of the distal tip 406 to secure the connection.

Example Methods of Use

For a given treatment session, the elongated member 102 can be nasally or orally inserted into the patient's body until the distal portion 102b of the elongated member 102 is positioned proximate a treatment site within the patient's pharynx. For example, the device 100 can be inserted through a nostril of a patient and advanced distally through the nasal cavity and nasopharynx until the conductive elements 108 at the distal portion 102b are positioned in apposition with a posterior wall of the pharynx. In some embodiments, one or both of the conductive elements 108 may be aligned with the nasopharynx, the oropharynx, and/or the laryngopharynx. In these and other embodiments, the conductive elements 108 are positioned within the pharynx (any of the nasopharynx, oropharynx, and laryngopharynx) in contact with a portion of the posterior pharyngeal wall opposite the C3/C4 vertebral junction.

In some embodiments, the elongated member 102 can comprise one or more indicators configured to facilitate insertion and positioning of the device 100 within the patient. For example, the indicator can comprise one or more visual markings that, when viewed through the patient's oral cavity, indicate the conductive elements 108 are properly positioned or that the elongated member 102 (and/or conductive elements 108) should be inserted further or withdrawn. In some embodiments, the indicator comprises one or more circumferential markings (such as one or more colored bands) printed on the elongated member 102.

When the conductive elements 108 are in a desired position, stimulation energy is delivered to the treatment site. In some embodiments, the delivered current is a unipolar square wave having an amplitude between 1 mA and 50 mA, a frequency of 5 Hz, and a pulse duration of 200 μS. Each treatment session can have a duration between 5 minutes and 20 minutes. For example, the treatment session can have a duration of 10 minutes. In some embodiments, a patient can undergo a single treatment per day over the course of multiple days of treatment. For example, a patient can undergo one treatment session per day for three to six consecutive days. In some embodiments, the patient may undergo multiple treatment sessions per day and/or per week. Still, other current parameters and treatment parameters are possible.

For any of the foregoing embodiments, the elongated member 102 can be moveable between an insertion state in which the elongated member 102 is more flexible and/or easier to maneuver and a treatment state in which the turns and tensions in the elongated member 102 are fixed into an orientation that actively pushes the conductive elements 108 against the posterior wall. The elongated member 102 can be transformed from the insertion state to the treatment state via mechanical actuation by a user, such as pulling or pushing a cable, a rod, and/or a wire, turning a screw, a knob, or other actuator, pushing a button or other actuator, etc. In some embodiments, the device 100 includes a locking member that can be actuated to hold the elongated member 102 in the insertion state and/or the treatment state and released to allow movement of the elongated member 102 between the two states.

CONCLUSION

Although many of the embodiments are described above with respect to systems, devices, and methods for electrically stimulating a pharynx of a patient to treat a patient suffering from dysphagia, the technology is applicable to other applications and/or other approaches. For example, the device may be used to treat other conditions, or used to apply a different form of energy (such as ablation energy). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

As used herein, the terms "generally," "substantially," "about," and similar terms are used as terms of approximation and not as terms of degree, and are intended to account for the inherent variations in measured or calculated values that would be recognized by those of ordinary skill in the art.

I claim:

1. A device comprising:
an elongated member for nasal insertion into a patient's pharynx, the elongated member having a proximal portion, a distal portion, and a longitudinal axis, wherein the elongated member comprises a first region having a first stiffness and a second region proximal of the first region along the longitudinal axis, and wherein the second region has a second stiffness less than the first stiffness; and
a conductive element carried by the distal portion of the elongated member and configured to be electrically coupled to an energy source for delivering electric current to nerves proximate the pharynx,
wherein, when the elongated member is inserted through a nostril of the patient such that the distal portion is positioned at a treatment site within the pharynx, the conductive element is placed in apposition with the pharyngeal wall, the first region extends along at least a portion of the nasal cavity and at least a portion of the nasopharynx, and the second region is positioned at or proximal of the patient's nostril.

2. The device of claim 1, wherein the elongated member further comprises a third region distal of the first region along the longitudinal axis of the elongated member, and wherein the third region has a stiffness different than the stiffness of the first region.

3. The device of claim 1, further comprising a distal element at the distal portion of the elongated member and positioned distal to the first region, wherein the distal element has a curved distal end portion configured to guide the distal portion of the elongated member around the nasopharynx and into the oropharynx during insertion of the device through the nasal cavity.

4. The device of claim 1, wherein the conductive element is positioned along the first region of the elongated member.

5. The device of claim 1, wherein a sidewall of the elongated member comprises a structural member coextensive with the first and second regions, wherein the structural member is at least one of a coil or a braid.

6. The device of claim 1, wherein the device further comprises a structural member disposed within a lumen of the elongated member, wherein the structural member is at least one of a coil or a braid.

7. The device of claim 5, wherein the structural member comprises a coil having a first length with a first pitch and a second length with a second pitch different than the first pitch.

8. The device of claim 7, wherein the first length of the coil is coextensive with the first region of the shaft and the second length of the coil is coextensive with the second region of the shaft.

9. The device of claim 5, wherein the structural member comprises a braid having a variable stiffness along its length.

10. The device of claim 1, wherein the first region of the elongated member is configured to be positioned proximal to an upper esophageal sphincter of the patient when the conductive element is delivering electric current to the nerves.

11. The device of claim 1, wherein the elongated member has a closed distal end.

12. The device of claim 1, wherein the electric current delivered to the nerves proximate the pharynx is configured to treat dysphagia.

13. A device comprising:
an elongated member for nasal insertion into a patient's pharynx, the elongated member having a proximal portion, a distal portion, a biasing region between the proximal and distal portions, and a longitudinal axis, wherein the elongated member has a variable stiffness along the longitudinal axis; and
a conductive element carried by the distal portion of the elongated member and configured to be electrically coupled to an energy source for delivering electric current to nerves proximate the pharynx,
wherein the biasing region is biased towards a straight configuration such that, when the elongated member is inserted through a nostril of the patient and the biasing region bends around the nasopharyngeal junction, the elongated member applies a restoring force that holds the conductive element in contact with a posterior region of the pharyngeal wall.

14. The device of claim 13, wherein a stiffness of the elongated member along the biasing region is greater than a stiffness of a portion of the elongated member proximal of the biasing region.

15. The device of claim 14, wherein the portion of the elongated member is configured to be positioned at or proximal of the patient's nostril when the elongated member is positioned within the pharynx and delivering electric current.

16. The device of claim 13, further comprising a distal element at the distal portion of the elongated member and positioned distal to the second region, wherein the distal element has a curved distal end portion configured to guide the distal portion of the elongated member around the nasopharynx and into the oropharynx during insertion of the device through the nasal cavity.

17. The device of claim 13, wherein the conductive element is positioned along the biasing region of the elongated member.

18. The device of claim 13, wherein a sidewall of the elongated member comprises a structural member coextensive with the biasing region, wherein the structural member is at least one of a coil or a braid.

19. The device of claim 13, wherein the distal portion of the elongated member is configured to be positioned proximal to an upper esophageal sphincter of the patient when the conductive element is delivering electric current to the nerves.

20. The device of claim 13, wherein the elongated member has a closed distal end.

21. The device of claim 13, wherein the electric current delivered to the nerves proximate the pharynx is configured to improve a swallowing reflex of the patient.

22. A method comprising:
inserting an elongated member through a nostril of a patient, the elongated member comprising a first region having a first stiffness and a second region having a second stiffness less than the first stiffness;
advancing the elongated member through the nasal cavity and into the pharynx such that a distal portion of the elongated member is positioned in the pharynx, wherein, when the distal portion is positioned in the pharynx, the first region spans a nasopharyngeal junction and the second region is positioned at or proximal of the patient's nostril; and stimulating nerves proximate a treatment site via a conductive element carried by the distal portion of the elongated member.

23. The method of claim 22, further comprising urging the conductive element into contact with a posterior wall of the pharynx via a restoring force provided by the first region.

24. The method of claim 22, wherein the distal portion of the elongated member does not extend distally through the upper esophageal sphincter.

25. The method of claim 22, wherein stimulation of the nerves proximate the treatment site improves a swallowing reflex of the patient.

* * * * *